United States Patent
Hercouet et al.

(10) Patent No.: US 10,765,615 B2
(45) Date of Patent: Sep. 8, 2020

(54) USE OF PARTICULAR PYRIDINIUM SALTS FOR THE TREATMENT OF KERATIN SUBSTANCES, COMPOSITIONS AND IMPLEMENTATION METHODS

(71) Applicant: L'OREAL, Paris (FR)

(72) Inventors: Leila Hercouet, Neuilly Plaisance (FR); Stephane Sabelle, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/536,731

(22) PCT Filed: Dec. 21, 2015

(86) PCT No.: PCT/EP2015/080850
§ 371 (c)(1),
(2) Date: Jun. 16, 2017

(87) PCT Pub. No.: WO2016/097413
PCT Pub. Date: Jun. 23, 2016

(65) Prior Publication Data
US 2017/0340543 A1      Nov. 30, 2017

(30) Foreign Application Priority Data
Dec. 19, 2014   (FR) .................................... 14 63028

(51) Int. Cl.
| *A61K 8/49* | (2006.01) |
| *A61K 8/22* | (2006.01) |
| *A61Q 5/08* | (2006.01) |
| *C07D 213/20* | (2006.01) |
| *C07D 213/50* | (2006.01) |
| *A61K 8/46* | (2006.01) |
| *C07C 309/30* | (2006.01) |

(52) U.S. Cl.
CPC .............. *A61K 8/4926* (2013.01); *A61K 8/22* (2013.01); *A61K 8/466* (2013.01); *A61Q 5/08* (2013.01); *C07C 309/30* (2013.01); *C07D 213/20* (2013.01); *C07D 213/50* (2013.01)

(58) Field of Classification Search
None
See application file for complete search history.

(56) References Cited

U.S. PATENT DOCUMENTS

| 6,518,407 B1 | 2/2003 | Brock et al. |
| 2009/0320216 A1 | 12/2009 | Greaves et al. |
| 2011/0047712 A1* | 3/2011 | Gross .................. A61Q 5/08 8/111 |

FOREIGN PATENT DOCUMENTS

| FR | 2912140 A1 | 8/2008 |
| JP | 2011-184490 | 9/2011 |
| JP | 5433933 B2 | 3/2014 |
| WO | 02/18311 A1 | 3/2002 |
| WO | 2013/175002 A2 | 11/2013 |

OTHER PUBLICATIONS

Decision of Refusal for Japanese Patent Application No. 2017-533263, dated Nov. 19, 2018 (English Translation).
International Search Report for PCT/EP2015/080850, dated Feb. 15, 2016.
Dreser, H., "Ueber das Additionsprodukt von Pyridin mit Monochloraceton," Archiv Der Pharmazie, vol. 232, No. 3, 1894, pp. 183-186.
Kakehi, A., et al., "Preparation of New Nitrogen-bridged Heterocycles. 21. 1) A Facile Synthesis of 2-Indolizinethiols Usinge New Protecting Groups," Bulletin, Chemical Society of Japan, Mar. 1990, pp. 829-834.
Peng, Y., et al., "Bis(1-acetonylpyridinium) Pyridinium Hexaiodobismuth(III)," ACTA Crystallographica Section C, Crystal Structure Communications, vol. 56, No. 5, May 15, 2000, pp. e183-e184.
Saxena, J.P., et al., "Reaction of Iodine and Some Heterocyclic Tertiary Bases With Acetone and Methyl Isobutyl Ketone*," Australian Journal of Chemistry, 1967, pp. 1771-1772.
Semenov, Viktor V., et al., "A General Synthetic Method for Azollum and Azinium Dinitromethylldest," Mendeleev Communication, ScienceDirect, 1993, 3(2), pp. 58-60.
Zhang, Y., et al., "Dicationic Electrophilic Systems: The Activation of Carbocations and Carboxonium Ions by Pyridinium Groups and Related Heteroxycles," Tetrahedron Letters, vol. 43, No. 38, Sep. 16, 2002, pp. 6841-6844.
Zhang, X., et al., "A One-Step Approach to 1-(Fluoroalkyl)indolizine Derivatives," Laboratory of Organofluorine Chemistry, Shanghai Institute of Organic Chemistry, Synthesis 1999, No. 1, pp. 51-54.

* cited by examiner

*Primary Examiner* — Kevin S Orwig
(74) *Attorney, Agent, or Firm* — The Marbury Law Group, PLLC

(57) ABSTRACT

The present invention relates to the use of one or more particular pyridinium salts for the treatment of keratin substances, particularly human keratin fibres such as hair. The invention also relates to a method for the treatment of keratin substances using said salts and optionally one or more chemical oxidizing agents. The invention also relates to a composition for lightening keratin substances comprising one or more pyridinium salts as defined hereinafter and one or more chemical oxidizing agents. The present invention also relates to one or more particular pyridinium salts and also to compositions containing them, especially compositions comprising a physiologically acceptable medium.

11 Claims, No Drawings

USE OF PARTICULAR PYRIDINIUM SALTS FOR THE TREATMENT OF KERATIN SUBSTANCES, COMPOSITIONS AND IMPLEMENTATION METHODS

CROSS REFERENCE TO RELATED APPLICATIONS

This is a national stage application of PCT/EP2015/080850, filed internationally on Dec. 21, 2015, which claims priority to French Application No. 1463028, filed on Dec. 19, 2014, both of which are incorporated by reference herein in their entireties.

The present invention relates to the use of one or more particular pyridinium salts for the treatment of keratin substances, particularly human keratin fibres such as hair. The invention also relates to a method for the treatment of keratin substances using said salts and optionally in the presence of one or more chemical oxidizing agents.

The invention also relates to a composition for lightening keratin substances comprising one or more pyridinium salts as defined hereinafter and one or more chemical oxidizing agents.

The present invention also relates to one or more particular pyridinium salts and also to compositions containing them, especially compositions comprising a physiologically acceptable medium.

When a person wishes to change hair colour, in particular when she wishes to obtain a lighter colour than her original colour, it is often necessary to proceed with hair lightening or bleaching. To do this, lightening or bleaching products are used. This step is optionally combined with a hair colouring step.

It is known to lighten or bleach keratin substances, in particular keratin fibres, and especially human keratin fibres such as hair, with lightening or bleaching compositions containing one or more chemical oxidizing agents.

Among these chemical oxidizing agents used conventionally, mention may be made of hydrogen peroxide, compounds that can produce hydrogen peroxide by hydrolysis, such as urea peroxide or persalts such as perborates, percarbonates and persulfates, hydrogen peroxide and persulfates being particularly preferred.

The role of the chemical oxidizing agent is to degrade the melanin of the hair, which, depending on the nature of the oxidizing agent and the pH conditions, leads to more or less pronounced lightening of the fibres.

The lightening or bleaching compositions are presented in anhydrous or aqueous form and in various different delivery forms: for example in the form of powders, creams, gels, foams or pastes, containing alkaline compounds such as alkaline amines or silicates, and a peroxygenated reagent such as ammonium or alkali metal persulfates, perborates or percarbonates, that are diluted at the time of use with an aqueous hydrogen peroxide composition.

The lightening or bleaching compositions may also result from mixing, at the time of use, an anhydrous powder containing the peroxygenated reagent with an aqueous composition containing the alkaline compounds and another aqueous composition containing hydrogen peroxide.

Moreover, the keratin substances may also be bleached using a conventional method involving putting on said substances an aqueous composition comprising at least one oxidizing agent.

Thus, for relatively mild lightening, the oxidizing agent is generally hydrogen peroxide. When greater lightening is desired, peroxygenated salts, for instance persulfates, are usually used in the presence of hydrogen peroxide.

To make a lightening or bleaching product for keratin substances that is more effective in terms of lightening and/or speed, it is currently necessary to combine hydrogen peroxide with an alkaline agent or persulfate salts with a basic pH to deliver adequate formation of active oxygen.

However, such a combination commonly causes degradation of keratin substances, in particular keratin fibres, and may possibly lead to varying degrees of skin irritation.

Accordingly a real need exists to use compounds that do not present the drawbacks mentioned hereinbefore, i.e. that can produce, in safer conditions than persulfates, powerful lightening, especially of keratin fibres, while minimizing their degradation.

The Applicant has therefore discovered, in a surprising manner, that using one or more pyridinium salts having formula (I), as defined hereinafter, allows in particular the improvement of the oxidizing power of the hydrogen peroxide, which delivers greater lightening of keratin substances, especially keratin fibres, while minimizing their degradation.

In other words, implementing compounds having formula (I) according to the invention improves the activity of the hydrogen peroxide without having to increase its concentration or having to use persulfate salts at high concentrations, which minimizes the problems of sensitization of keratin substances.

Accordingly, the use of pyridinium salt(s) according to the use leads to greater lightening of keratin substances without having to increase the strength of the oxidizing agent.

In other words, using pyridinium salt(s) according to the invention boosts the oxidizing activity of chemical oxidizing agents, in particular hydrogen peroxide, leading to improved lightening of the keratin substances compared to using the chemical oxidizing agent alone.

What is more, the pyridinium salts having formula (I) in combination, in particular with hydrogen peroxide, lead to more powerful lightening of keratin substances than pyridinium salts, used under the same conditions, but that are structurally different than those of the invention.

Therefore the present invention relates in particular to the use for the treatment of keratin substances, preferably keratin fibres, in particular human keratin fibres such as hair, of one or more compounds having formula (I) and the addition salts and solvates thereof:

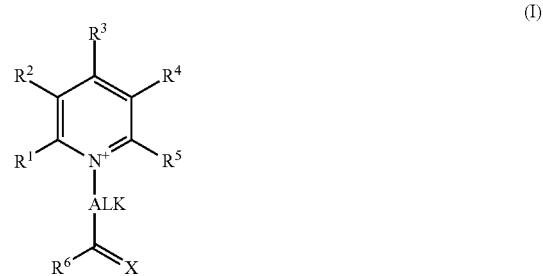

(I)

Formula (I) in which:
$R^1$, $R^2$, $R^3$, $R^4$ and $R^5$, which may be identical or different, represent:
  a hydrogen or halogen atom;
  a linear or branched $C_1$-$C_{10}$ alkyl substituent, optionally substituted by one or more hydroxyl, $C_1$-$C_{10}$ alkoxy, $C_1$-$C_4$ hydroxyalkyl and —$NR^7R^8$ groups;

a linear or branched $C_1$-$C_{10}$ alkoxy substituent, optionally substituted by one or more hydroxyl, $C_1$-$C_{10}$ alkoxy, $C_1$-$C_{10}$ hydroxyalkyl and —$NR^7R^8$ groups;

a —$CO_2R^9$ substituent, a —$COR^{10}$ substituent, or two adjacent substituents $R^1$ and $R^2$, $R^2$ and $R^3$, $R^3$ and $R^4$ and/or $R^4$ and $R^5$ can form together with the carbon atoms to which they are attached a cycloalkyl group including 5 to 10 members or an aryl group including 6 to 10 members, it being understood that said cycloalkyl or aryl group optionally comprises one or more heteroatoms and is optionally substituted by one or more halogen atoms, one or more linear or branched $C_1$-$C_{10}$ alkyl substituents, one or more linear or branched $C_1$-$C_{10}$ alkoxy substituents, one or more hydroxyl groups, one or more $C_1$-$C_4$ hydroxyalkyl groups and one or more —$NR^7R^8$ groups;

ALK represents a linear or branched, saturated or unsaturated $C_1$-$C_{10}$ alkyl substituent;

$R^6$ represents:
  a hydrogen or halogen atom,
  a linear or branched, saturated or unsaturated $C_1$-$C_{10}$ alkyl substituent, optionally interrupted by one or more heteroatoms chosen from oxygen and nitrogen and/or optionally substituted by one or more hydroxyl, $C_1$-$C_{10}$ alkoxy, $C_1$-$C_4$ hydroxyalkyl and —$NR^7R^8$ groups;
  an aryl substituent including 5 to 12 members optionally substituted by one or more halogen atoms, one or more linear or branched $C_1$-$C_{10}$ alkyl substituents, one or more linear or branched $C_1$-$C_{10}$ alkoxy substituents, one or more hydroxyl groups, one or more $C_1$-$C_4$ hydroxyalkyl groups and one or more —$NR^7R^8$ groups;

X represents a heteroatom chosen from an oxygen atom or a sulfur atom, or a —$NR^{11}$ substituent;

$R^7$, $R^8$, $R^9$, $R^{10}$, and $R^{11}$, which may be identical or different, denote a hydrogen atom or a linear or branched $C_1$-$C_{10}$ alkyl substituent optionally substituted with one or more hydroxyl or $C_1$-$C_{10}$ alkoxy, $C_1$-$C_4$ hydroxyalkyl and amino groups;

being understood that one of the substituents $R^1$ or $R^5$ may form with the substituent $R^6$ a heterocycle comprising 5 to 8 members optionally substituted in particular by one or more oxo groups;

Q- represents an anion or a mixture of organic or inorganic anions that ensure electroneutrality in compounds having formula (I).

The compound(s) having formula (I) defined in this way therefore correspond to pyridinium salts and act as oxidation activators.

The compound(s) having formula (I) according to the invention may be used in the presence of one or more chemical oxidizing agents for lightening keratin substances, preferably keratin fibres, in particular human keratin fibres such as hair.

Therefore the present invention also relates in particular to the treatment of keratin substances, preferably keratin fibres, in particular human keratin fibres such as hair, consisting in applying to said substances one or more compounds having formula (I) and the addition salts and solvates thereof.

Preferably, the method according to the invention consists in applying said compounds having formula (I) and one or more chemical oxidizing agents.

Moreover, the invention relates to a composition for lightening keratin substances, preferably keratin fibres, in particular human keratin fibres such as hair, comprising one or more compounds having formula (I) and the addition salts and solvates thereof, and one or more chemical oxidizing agents.

In the same way, the invention also relates to the use of said composition for lightening keratin substances, preferably keratin fibres, in particular human keratin fibres such as hair.

In addition, the present invention relates to one or more particular compounds having formula (II) and the addition salts and solvates thereof such as hydrates:

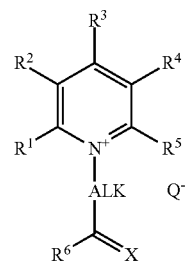

(II)

Formula (II) in which:

$R^1$ and $R^5$ represent a hydrogen atom;

$R^2$ and $R^4$, which may be identical or different, represent:
  a hydrogen atom,
  a linear or branched $C_2$-$C_{10}$ alkyl substituent, optionally substituted by one or more hydroxyl, $C_1$-$C_{10}$ alkoxy, and —$NR^7R^8$ groups,
  a linear or branched $C_1$-$C_{10}$ alkoxy substituent, optionally substituted by one or more hydroxyl, $C_1$-$C_{10}$ alkoxy, and —$NR^7R^8$ groups,
  a —$CO_2H$ substituent,
  a —$CO_2R^9$ substituent,
  a —$COR^{10}$ substituent, $R^3$ represents:
  a hydrogen atom;
  a linear or branched $C_2$-$C_{10}$ alkyl substituent, optionally substituted by one or more hydroxyl, $C_1$-$C_{10}$ alkoxy and —$NR^7R^8$ groups,
  a linear or branched $C_1$-$C_{10}$ alkoxy substituent, optionally substituted by one or more hydroxyl, $C_1$-$C_{10}$ alkoxy, $C_1$-$C_4$ hydroxyalkyl and $NR^7R^8$ groups;
  a —$CO_2R^9$ substituent,
  a —$COR^{10}$ substituent, ALK represents a methylene substituent, $R^6$ represents a methyl substituent, $R^7$ and $R^8$, which may be identical or different, denote a hydrogen atom or a linear or branched $C_1$-$C_{10}$ alkyl substituent optionally substituted with one or more hydroxyl or $C_1$-$C_{10}$ alkoxy and amino groups;

$R^9$ and $R^{10}$, which may be identical or different, denote a linear or branched $C_1$-$C_{10}$ alkyl substituent optionally substituted with one or more hydroxyl or $C_1$-$C_{10}$ alkoxy and amino groups;

Q- represents an anion or a mixture of organic or inorganic anions that ensure electroneutrality in compounds having formula (II), being understood that formula (II) cannot represent the following compound having formula (III):

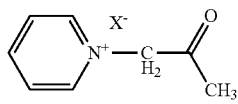 (III)

Formula (III) in which X⁻ represents an anion chosen from chloride ion (Cl⁻), bromide ion (Br⁻), iodide ion (I⁻), perchlorate ion ($ClO_4^-$), methosulfate ion ($MeSO_4^-$) and hexafluorophosphate ion ($PF_6^-$).

In the same way, the present invention also relates to a composition comprising said compound(s) having formula (II) and the addition salts and solvates thereof.

Other subjects, characteristics, aspects and advantages of the invention will emerge even more clearly on reading the description and the examples that follow.

In that which follows and unless otherwise indicated, the limits of a range of values are included within this range, in particular in the expressions "of between" and "ranging from . . . to . . . ".

Moreover, the expression "at least one" used in the present description is equivalent to the expression "one or more". In addition, the expression "at least two" is equivalent to the expression "two or more".

The term "anion or mixture of anions ensuring electroneutrality of compounds having formulae (I) and (II)" means an anion or an anionic group derived from an organic or inorganic acid salt which counterbalances the cationic charge of the compound; more particularly, the anionic counterion is chosen from: i) halides such as chloride or bromide; ii) nitrates; iii) sulfonates, including $C_1$-$C_6$ alkylsulfonates: Alk-S(O)₂O— such as methanesulfonate or mesylate and ethanesulfonate; iv) arylsulfonates: Ar—S(O)₂O— such as benzenesulfonate and toluenesulfonate or tosylate; v) citrate; vi) succinate; vii) tartrate; viii) lactate; ix) alkyl sulfates: Alk-O—S(O)O— such as methyl sulfate and ethyl sulfate; x) aryl sulfates: Ar—O—S(O)O— such as benzene sulfate and toluene sulfate; xi) alkoxy sulfates: Alk-O—S(O)₂O— such as methoxy sulfate and ethoxy sulfate; xii) aryloxy sulfates: Ar—O—S(O)₂O—, xiii) phosphates O=P(OH)₂—O—, O=P(O⁻)₂—OH, O=P(O⁻)₃, HO—[P(O)(O—)]w-P(O)(O⁻)₂ with w being an integer; xiv) acetate; xv) triflate; and xvi) borates such as tetrafluoroborate, xvii) disulfate (O=)₂S(O⁻)₂ or $SO_4^{2-}$ and monosulfate $HSO_4^-$; xviii) carbonate $CO_3^{2-}$ or hydrogen carbonate $HCO_3^-$; the anionic counterion, derived from an organic or inorganic acid salt, ensures the electrical neutrality of the molecule; thus, it is understood that when the anion comprises several anionic charges, then the same anion can serve for the electrical neutrality of several cationic groups in the same molecule or else may serve for the electrical neutrality of several molecules.

Addition salts of compounds having formulae (I) and (II) according to the invention are understood therefore to be salts of addition with an organic or inorganic acid, and salts of addition with an organic or inorganic base.

The addition salts of the compounds having formulae (I) and (II) according to the invention are in particular chosen from addition salts with an acid, such as hydrochlorides, hydrobromides, sulfates, citrates, succinates, tartrates, lactates, tosylates, benzenesulfonates, methanesulfonates, phosphates and acetates, and the addition salts with a base such as sodium hydroxide, potassium hydroxide, ammonia, amines or alkanolamines.

Moreover, the solvates of the compounds having formulae (I) and (II) according to the invention more particularly represent the hydrates of said compounds and/or the combination of said compounds with a linear or branched $C_1$ to $C_4$ alcohol such as methanol, ethanol, isopropanol or n-propanol. Preferably, the solvates are hydrates.

Use of the Compounds Having Formula (I)

Q⁻ represents an anion or a mixture of organic or inorganic anions that ensure electroneutrality in compounds having formula (I).

Preferably, Q⁻ is an anion chosen from halides, in particular chloride, bromide and iodide, sulfates, phosphates; carbonate; hydrogen carbonate; methanesulfonate; para-toluenesulfonate; camphorsulfonate; tartrate; citrate; lactate; acetate.

More preferentially, Q⁻ is an anion chosen from para-toluenesulfonate and halides, particularly chloride.

Preferably, X represents an oxygen atom.

Preferably, ALK represents a linear $C_1$-$C_{10}$ alkylene substituent, a linear $C_2$-$C_{10}$ alkenylene substituent or a linear alkynylene $C_2$-$C_{10}$ substituent.

Preferentially, ALK represents a linear $C_1$-$C_{10}$ alkylene substituent, more preferentially a linear $C_1$-$C_4$ alkylene substituent, especially a methylene (—CH₂—) substituent.

Preferably, $R^1$ and $R^5$ represent a hydrogen atom.

Preferably, $R^2$ and $R^4$, which may be identical or different, represent:

a hydrogen atom;

a linear or branched $C_2$-$C_{10}$ alkyl substituent, optionally substituted by one or more hydroxyl, $C_1$-$C_{10}$ alkoxy, and —NR⁷R⁸ groups with $R^7$ and $R^8$ having the definition previously indicated in formula (I);

a linear or branched $C_1$-$C_{10}$ alkoxy substituent, optionally substituted by one or more hydroxyl, $C_1$-$C_{10}$ alkoxy, and —NR⁷R⁸ groups with $R^7$ and $R^8$ having the definition previously indicated in formula (I);

a —CO₂H substituent, and a —CO₂R⁹ substituent a —COR¹⁰ substituent with $R^{10}$ having the definition previously indicated in formula (I).

More preferentially, $R^2$ and $R^4$ represent a hydrogen atom or a linear $C_1$-$C_4$ alkyl group, in particular a methyl group.

Preferably, $R^3$ represents:

a hydrogen atom;

a linear or branched $C_2$-$C_{10}$ alkyl substituent, optionally substituted by one or more hydroxyl, $C_1$-$C_{10}$ alkoxy and —NR⁷R⁸ groups with $R^7$ and $R^8$ having the definition previously indicated in formula (I);

a linear or branched $C_1$-$C_{10}$ alkoxy substituent, optionally substituted by one or more hydroxyl, $C_1$-$C_{10}$ alkoxy, $C_1$-$C_4$ hydroxyalkyl and —NR⁷R⁸ with $R^7$ and $R^8$ having the definition previously indicated in formula (I), a —CO₂R⁹ substituent with $R^9$ having the definition previously indicated in formula (I), and a —COR¹⁰ substituent with $R^{10}$ having the definition previously indicated in formula (I).

More preferentially, $R^3$ represents a hydrogen atom or a —COR¹⁰ substituent with $R^{10}$ denoting a linear $C_1$-$C_{10}$ alkyl substituent, particularly a linear $C_1$-$C_4$ alkyl substituent.

Even more preferably, $R^3$ represents a hydrogen atom or a —COCH3 substituent.

Preferably, $R^6$ represents:

a hydrogen atom;

a linear $C_1$-$C_{10}$ alkyl substituent, a linear $C_2$-$C_{10}$ alkenyl substituent or a linear $C_2$-$C_{10}$ alkynyl substituent optionally interrupted by one or more heteroatoms chosen from oxygen and nitrogen and/or optionally substituted by one or more hydroxyl, $C_1$-$C_1^0$ alkoxy, $C_1$-$C_4$ hydroxyalkyl and —$NR^7R^8$ with $R^7$ and $R^8$ having the definition previously indicated in formula (I).

More preferentially, $R^6$ represents a linear $C_1$-$C_6$ alkyl substituent and more particularly a linear $C_1$-$C_4$ alkyl substituent such as methyl or ethyl, more preferentially methyl.

Preferably, $R^7$, $R^8$, $R^9$ and $R^{10}$, which may be identical or different, denote a linear or branched $C_1$-$C_{10}$ alkyl substituent optionally substituted with one or more hydroxyl, $C_1$-$C_{10}$ alkoxy and amino groups.

More preferentially, $R^7$, $R^8$, $R^9$ and $R^{10}$, which may be identical or different, denote a linear $C_1$-$C_4$ alkyl substituent.

Preferably, $R^{11}$ represents a hydrogen atom.

According to one embodiment, $R^1$, $R^2$, $R^3$, $R^4$ and $R^5$ represent a hydrogen atom.

According to another embodiment, $R^1$ and $R^5$ represent a hydrogen atom, $R^2$ and $R^4$ represent a hydrogen atom or a linear $C_1$-$C_4$ alkyl substituent, in particular a methyl substituent, $R^3$ represents a hydrogen atom or a —$COR^{10}$ substituent with $R^{10}$ denoting a linear $C_1$-$C_4$ alkyl substituent, $R^6$ represents a linear $C_1$-$C_6$ alkyl substituent, particularly a linear $C_1$-$C_4$ alkyl substituent.

In accordance with this embodiment, X is preferably an oxygen atom.

In accordance with this embodiment, ALK represents a linear $C_1$-$C_{10}$ alkylene substituent, more preferentially a linear $C_1$-$C_4$ alkylene substituent, especially a methylene (—$CH_2$—) substituent.

Preferably, the compound(s) having formula (I) as defined hereinbefore is or are chosen from the compound(s) having formula (II) and the addition salts and solvates thereof:

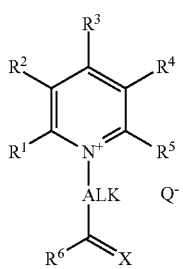

(II)

Formula (II) in which:
$R^1$ and $R^5$ represent a hydrogen atom;
$R^2$ and $R^4$, which may be identical or different, represent:
  a hydrogen atom,
  a linear or branched $C_2$-$C_{10}$ alkyl substituent, optionally substituted by one or more hydroxyl, $C_1$-$C_{10}$ alkoxy and —$NR^7R^8$ groups,
  a linear or branched $C_1$-$C_{10}$ alkoxy substituent, optionally substituted by one or more hydroxyl, $C_1$-$C_{10}$ alkoxy and —$NR^7R^8$ groups,
  a —$CO_2H$ substituent,
  a —$CO_2R^9$ substituent,
  a —$COR^{10}$ substituent,
—$R^3$ represents:
  a hydrogen atom;
  a linear or branched $C_2$-$C_{10}$ alkyl substituent, optionally substituted by one or more hydroxyl, $C_1$-$C_{10}$ alkoxy, and —$NR^7R^8$ groups,
  a linear or branched $C_1$-$C_{10}$ alkoxy substituent, optionally substituted by one or more hydroxyl, $C_1$-$C_{10}$ alkoxy, $C_1$-$C_4$ hydroxyalkyl and —$NR^7R^8$ groups;
  a —$CO_2R^9$ substituent,
  a —$COR^{10}$ substituent,
ALK represents a methylene substituent,
$R^6$ represents a methyl substituent,
$R^7$ and $R^8$, which may be identical or different, denote a hydrogen atom or a linear or branched $C_1$-$C_{10}$ alkyl substituent optionally substituted with one or more hydroxyl or $C_1$-$C_{10}$ alkoxy and amino groups;
$R^9$ and $R^{10}$, which may be identical or different, denote a linear or branched $C_1$-$C_{10}$ alkyl substituent optionally substituted with one or more hydroxyl or $C_1$-$C_{10}$ alkoxy and amino groups;
$Q^-$ represents an anion or a mixture of organic or inorganic anions that ensure electroneutrality in compounds having formula (II).

Preferentially, in formula (II), $R^2$ and $R^4$, which may be identical or different, represent a hydrogen atom or a linear $C_1$-$C_4$ alkyl substituent, in particular a methyl substituent.

Preferentially, in formula (II), $R^3$ represents a hydrogen atom or a —$COR^{10}$ substituent with $R^{10}$ denoting a linear $C_1$-$C_{10}$ alkyl substituent, particularly a linear $C_1$-$C_4$ alkyl substituent.

Preferentially, in formula (II), $Q^-$ is an anion chosen from para-toluenesulfonate and halides, particularly chloride.

The compound(s) having formula (I) is or are preferentially chosen from the following compounds:

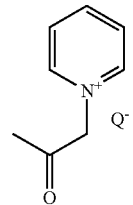

Salt of 1-(2-Oxo-propyl)pyridinium, with
$Q^-$ as defined previously, preferably: halide
such as $Cl^-$ (compound 1), or arylsulfonate
such as toluene-4-sulfonate
(compound 2)

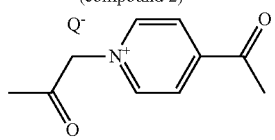

Salt of 4-Aetyl-1-(2-oxo-propyl)-pyridinium,
with $Q^-$ as defined previously, preferably:
halide such as
$Cl^-$ (compound 3)

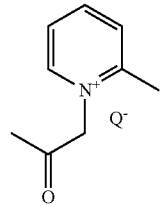

Salt of 2-Methyl-1-(2-oxo-propyl)pyridinium,
with $Q^-$ as defined previously, preferably:
halide such as
$Cl^-$ (compound 4)

and mixtures thereof.

Preferentially, the compound having formula (I) is 1-(2-oxo-propyl)pyridinium chloride (compound 1).

As indicated previously, the compound(s) having formula (I) according to the invention, preferably compounds 1 to 4, may be used in the presence of one or more chemical oxidizing agents for lightening keratin substances, preferably keratin fibres, in particular human keratin fibres such as hair.

The oxidizing agents are such as those described hereinafter.

Composition Containing Compounds Having Formula (I)

Accordingly, the invention relates to a composition comprising the compound(s) having formula (I), preferably the compounds having formula (II) as defined hereinbefore, and the addition salts and solvates thereof and one or more chemical oxidizing agents.

Preferably, the composition according to the invention comprises one or more compounds having formula (I) chosen from the 1-(2-oxo-propyl)pyridinium salt (compound 1 and 2), the 4-acetyl-1-(2-oxo-propyl)-pyridinium salt (compound 3), the 2-methyl-1-(2-oxo-propyl)-pyridinium salt (compound 4).

Preferably, the composition according to the invention comprises at least one compound chosen from salts of 1-(2-oxo-propyl)pyridinium (compound 1 and 2), particularly 1-(2-oxo-propyl)pyridinium chloride.

The composition according to the invention lightens keratin substances, in particular keratin fibres and preferably human keratin fibres such as hair, using less chemical oxidizing agent.

According to a particular embodiment of the invention, the dye composition comprises at least one chemical oxidizing agent. The term "chemical oxidizing agent" means an oxidizing agent other than atmospheric oxygen. The composition of the invention preferentially contains one or more chemical oxidizing agents.

The oxidizing agent(s) used in the invention are for example hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred.

More particularly, the chemical oxidizing agent(s) are chosen from hydrogen peroxide, urea peroxide, alkali metal bromates, peroxygenated salts, for instance persulfates or perborates, peracids and precursors thereof and alkali metal or alkaline-earth metal percarbonates. The chemical oxidizing agent(s) advantageously consist of hydrogen peroxide.

The compound(s) having formula (I) and the addition salts and solvates thereof may be present in the composition according to the invention in a content ranging from 0.01% to 10% by weight, preferably in a content by weight ranging from 0.5% to 2% by weight, relative to the total weight of the composition.

Preferentially, the chemical oxidizing agent is hydrogen peroxide.

According to one embodiment, the composition according to the invention comprises one or more compounds having formula (I), preferably having formula (II), and the addition salts and solvates thereof and at least one chemical oxidizing agent such as hydrogen peroxide.

In accordance with this embodiment, the composition preferably additionally comprises one or more persulfates.

In other words, the composition may preferentially comprise a mixture of hydrogen peroxide and persulfates.

According to one embodiment, the composition according to the invention comprises one or more compounds having formula (I), preferably having formula (II), and the addition salts and solvates thereof and hydrogen peroxide as chemical oxidizing agent; said composition being free of persulfates.

In accordance with these embodiments, the compound having formula (II) is a salt of 1-(2-oxo-propyl)pyridinium, preferably a 1-(2-oxo-propyl)pyridinium halide such as 1-(2-oxo-propyl)pyridinium chloride (compound 1).

The chemical oxidizing agent(s) may be present in the composition according to the invention in a content ranging from 0.5% to 9% by weight of the ready-to-use composition, preferably in a content by weight ranging from 1.5% to 9% by weight, relative to the total weight of the ready-to-use composition.

Preferably, the composition according to the invention may comprise one or more alkaline agents, in particular organic or inorganic alkaline agents.

The inorganic alkaline agent(s) are preferably chosen from aqueous ammonia, ammonium halides and particularly ammonium chloride, alkali metal carbonates or bicarbonates such as sodium or potassium carbonates and sodium or potassium bicarbonates, sodium hydroxide or potassium hydroxide, or mixtures thereof.

The organic alkaline agent(s) are preferably chosen from organic amines with a pKb at 25° C. of less than 12, preferably less than 10 and even more advantageously less than 6. It should be noted that it concerns the pKb corresponding to the functional group having the highest basicity. In addition, the organic amines do not comprise any alkyl or alkenyl fatty chain comprising more than ten carbon atoms.

The organic alkaline agent(s) are chosen, for example, from alkanolamines, oxyethylenated and/or oxypropylenated ethylenediamines, amino acids and the compounds having formula (III) below:

(III)

Formula (III) in which W is a divalent $C_1$-$C_6$ alkylene substituent optionally substituted with one or more hydroxyl groups or a $C_1$-$C_6$ alkyl substituent, and/or optionally interrupted with one or more heteroatoms such as O, or —NRu; Rx, Ry, Rz, Rt and Ru, which may be identical or different, represent a hydrogen atom or a $C_1$-$C_6$ alkyl, $C_1$-$C_6$ hydroxyalkyl or $C_1$-$C_6$ aminoalkyl substituent.

Examples of amines having formula (III) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl substituents.

Organic amines chosen from alkanolamines such as monoalkanolamines, dialkanolamines or trialkanolamines comprising one to three identical or different $C_1$-$C_4$ hydroxyalkyl substituents are in particular suitable for performing the invention.

Among the compounds of this type, mention may be made of monoethanolamine (MEA), diethanolamine, triethanolamine, mono isopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that can be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that may be used in the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine and salts thereof.

Advantageously, the amino acids are basic amino acids comprising an additional amine function optionally included in a ring or in a ureido function.

Such basic amino acids are preferably chosen from those corresponding to formula (IV) below, and also the salts thereof

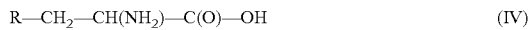

R—CH$_2$—CH(NH$_2$)—C(O)—OH  (IV)

in which R represents a group chosen from imidazolyl, preferably imidazolyl-4-yl; aminopropyl; aminoethyl; —(CH$_2$)$_2$NH—C(O)—NH$_2$; and —(CH$_2$)$_2$—NH—C(NH)—NH$_2$.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and balenine.

The organic amine may also be chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidino alanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the alkaline agent(s) present in the composition according to the invention are chosen from aqueous ammonia, alkanolamines, amino acids in neutral or ionic form, in particular basic amino acids, and preferably corresponding to those having formula (IV).

More preferentially, the alkaline agent(s) present in the composition according to the invention, are chosen from aqueous ammonia, alkanolamines, and mixtures thereof.

More preferentially, the alkaline agent(s) present in the composition according to the invention, are chosen from aqueous ammonia and ammonium chloride.

According to one particular embodiment of the invention, the alkaline agent(s) are inorganic.

According to one particular embodiment of the invention, the alkaline agent(s) are organic such alkanolamines particularly monoethanolamine.

The quantity of alkaline agent(s) present in the composition according to the invention may range from 0.01% to 30% by weight, and preferably from 0.1% to 20% by weight relative to the total weight of the composition.

The composition according to the invention has a pH greater than or equal to 4. Preferably, the pH of the composition according to the invention varies from 7 to 11, more preferentially from 8 to 10 and more preferentially from 8.5 to 9.5.

According to one embodiment, the composition according to the invention comprises one or more compounds having formula (II) and the addition salts and solvates thereof, one or more chemical oxidizing agents and one or more alkaline agents chosen from aqueous ammonia and ammonium halides such as ammonium chloride.

In accordance with this embodiment, the compound having formula (II) is preferably chosen from halides of 1-(2-oxo-propyl)pyridinium and more preferentially 1-(2-oxo-propyl)pyridinium chloride (compound 1).

In accordance with this embodiment, the chemical oxidizing agent is preferably hydrogen peroxide.

The composition according to the invention may optionally comprise one or more additives, different from the compounds of the invention and among which mention may be in particular made of organic solvents, cationic, anionic, nonionic, amphoteric polymers or mixtures thereof, antidandruff agents, anti-seborrhoea agents, agents for preventing hair loss and/or for promoting hair regrowth, vitamins and provitamins including panthenol, sunscreens, inorganic or organic pigments, sequestrants, plasticizers, solubilizers, acidifying agents, inorganic or organic thickeners, especially polymeric thickeners, opacifiers or pearlizing agents, antioxidants, hydroxyacids, fragrances, preservatives, pigments and ceramides.

Needless to say, a person skilled in the art will take care to select this or these optional additional compound(s) such that the advantageous properties intrinsically associated with the composition according to the invention are not, or are not substantially, adversely affected by the envisaged addition(s).

The above adjuvants may generally be present in an amount, for each of them, of between 0 and 20% by weight relative to the total weight of the composition.

The composition according to the invention preferentially comprises a physiologically acceptable medium.

For the purposes of the present invention, the term "physiologically acceptable medium" is intended to denote a medium that is suitable for the topical administration of a composition. A physiologically acceptable medium is preferentially a cosmetically or dermatologically acceptable medium, i.e. a medium that has no unpleasant odor or appearance, and that is entirely compatible with the topical administration route. In the present case, where the composition is intended for topical administration, that is to say for administration by application at the surface of the keratin material under consideration, such a medium is considered in particular to be physiologically acceptable when it does not cause stinging, tightness or redness unacceptable to the user.

Treatment Method According to the Invention

The treatment method for keratin substances consists in applying to said substances one or more compounds having formula (I) as defined hereinbefore optionally in the presence of one or more chemical oxidizing agents.

Preferably, the compound(s) having formula (I) according to the invention is or are applied in the presence of one or more chemical oxidizing agents, more preferentially hydrogen peroxide.

According to one embodiment, the treatment method consists in applying the composition as defined previously on keratin substances.

Preferably, the treatment method consists in applying the composition as defined previously on dry or wet keratin fibres. It is left in place on the fibres for a period, generally from 1 minute to 1 hour, preferably from 5 minutes to 30 minutes.

The temperature during the method is conventionally between room temperature (between 15 and 25° C.) and 80° C. and preferably between room temperature and 60° C.

Preferentially, the composition is applied at room temperature.

After the treatment, the keratin substances are optionally rinsed with water, optionally washed with a shampoo and then rinsed with water, before being dried or left to dry.

The composition according to the invention can be prepared by mixing at least two compositions.

The composition according to the invention may especially be obtained by mixing two compositions:
- a composition (A) comprising one or more compounds having formula (I) according to the invention, and
- a composition (B) comprising one or more chemical oxidizing agents.

Compounds Having Formula (II) and Corresponding Composition

As indicated previously, the present invention also relates to compounds having formula (II) as defined previously and the addition salts and solvates thereof, being understood that formula (II) cannot represent the compound having formula (III) as defined previously.

The compound having formula (II) is different from:
the following compound having formula (III):

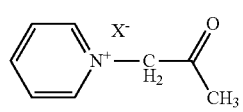
(III)

$X^-$ representing an anion chosen from chloride ion ($Cl^-$), bromide ion ($Br^-$), iodide ion ($I^-$), perchlorate ion ($ClO_4^-$), methosulfate ion ($MeSO_4^-$), hexafluorophosphate ion ($PF_6^-$), picrate ion ($C_6H_2N_3O_7^-$), mesylate ion ($CH_3SO_3^-$) and triflate ion ($CF_3SO_3^-$);

the following compound having formula (IV):

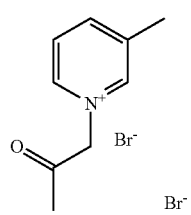
(IV)

the following compound having formula (V):

(V)

the compounds having formulas (VI) and (VII):

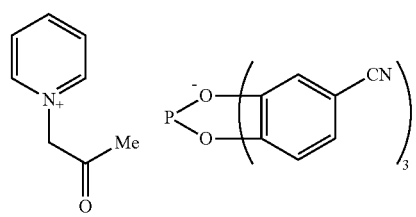
(VI)

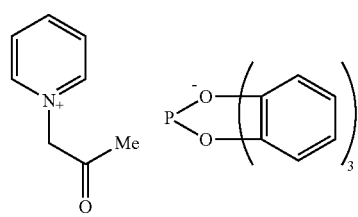
(VII)

the compound having formula (VIII):

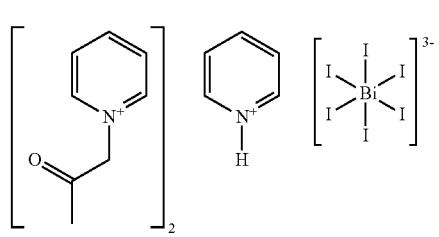
(VIII)

the compound having formula (IX):

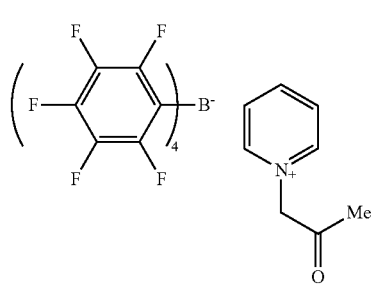
(IX)

Preferentially, in formula (II), $R^2$ and $R^4$, which may be identical or different, represent a hydrogen atom or a linear $C_1$-$C_4$ alkyl substituent, in particular a methyl substituent. More preferentially, $R^2$ and $R^4$ represent a hydrogen atom.

Preferentially, in formula (II), $R^3$ represents a hydrogen atom or a —$COR^{10}$ substituent with $R^{10}$ denoting a linear $C_1$-$C_{10}$ alkyl substituent, particularly a linear $C_1$-$C_4$ alkyl substituent.

More preferentially, $R^3$ represents a —$COR^{10}$ substituent with $R^{10}$ denoting a linear $C_1$-$C_4$ alkyl substituent, preferably —$COCH_3$.

Preferentially, in formula (II), $Q^-$ is an anion chosen from para-toluenesulfonate and halides, particularly chloride.

According to one particular embodiment of the invention, the compound having formula (II) represents the following compound:

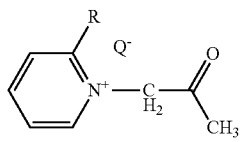

(II')

Formula (II') in which $Q^-$ is an anionic counterion as defined previously other than a chloride ion ($Cl^-$) and R represents a hydrogen atom or a methyl group, Preferably, the compound having formula (II) or (II') is 1-(2-oxo-propyl)-pyridinium toluene-4-sulfonate (compound 2) and 4-acetyl-1-(2-oxo-propyl)-pyridinium chloride (compound 3).

The invention also relates to a composition comprising one or more compounds having formula (II) or (II') as defined previously.

Preferably, the compound comprises one or more compounds having formula (II) or (II') chosen from 1-(2-oxo-propyl)-pyridinium toluene-4-sulfonate (compound 2) and 4-acetyl-1-(2-oxo-propyl)-pyridinium chloride (compound 3).

The compound(s) having formula (II) and the addition salts and solvates thereof may be present in the composition according to the invention in a content ranging from 0.01% to 10% by weight, preferably in a content ranging from 0.5% to 2% by weight, relative to the total weight of the composition.

The composition preferentially comprises a physiologically acceptable medium.

Method for Preparing the Compounds Having Formula (II)

The compounds having formula (II) may be obtained by quaternization of pyridine derivatives (1) with derivatives (2) with Q representing a leaving group such as a halogen atom, particularly chlorine, bromine and iodine, an alkylsulfonate or an arylsulfonate.

Such a reaction is generally carried out in the presence of a polar protic solvent, for example ethanol, and may be done at room temperature (27° C.) and is accelerated by heating (at solvent reflux).

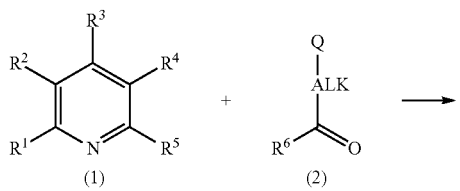

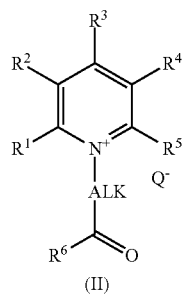

(II)

The compounds having formula (II) may also be obtained by simply exchanging the counteranion:

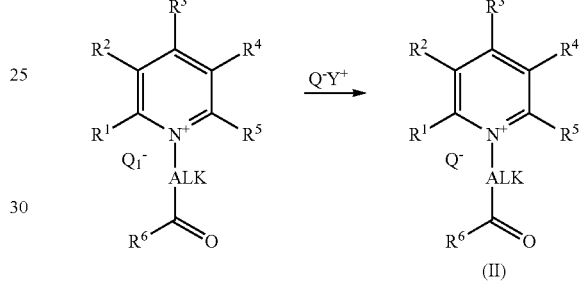

(II)

Particularly, these methods prepare 1-(2-oxo-propyl)-pyridinium toluene-4-sulfonate (compound 2) and 4-acetyl-1-(2-oxo-propyl)-pyridinium chloride (compound 3).

The present invention also relates to the use of one or more compounds having formula (I) as defined previously as oxidation activator.

Particularly, the compound(s) having formula (I) according to the invention are used in the presence of one or more chemical oxidizing agents to improve the lightening of keratin substances, preferably human keratin fibres such as hair.

In other words, the compound(s) having formula (I) according to the invention are used to improve the oxidizing activity of one or more chemical oxidizing agents.

Preferably, the chemical oxidizing agent is hydrogen peroxide.

The examples that follow serve to illustrate the invention without, however, being limiting in nature.

In these examples, the colour of the tresses was evaluated in the CIE L* a* b* system, using a Minolta Spectrophotometer CM2600D colourimeter.

In this L* a* b* system, the three parameters denote, respectively, the colour intensity (L*), the green/red colour axis (a*) and the blue/yellow colour axis (b*). The higher the value of L*, the lighter the colour. The higher the value of a*, the redder the colour and the higher the value of b*, the yellower the colour.

EXAMPLES

Example 1

Synthesis of 4-Acetyl-1-(2-oxo-propyl)-pyridinium chloride (Compound 3)

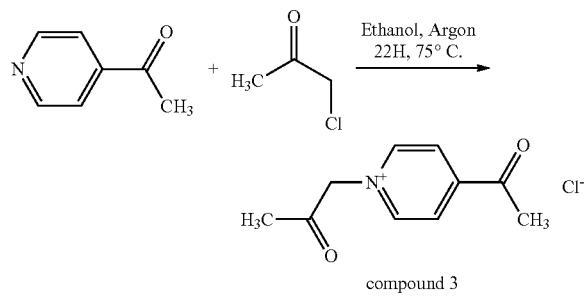

compound 3

To a solution of 0.5 g of 4-acetylpyridine (4.1 mmoles) in 2.5 g of absolute ethanol heated to 70° C. is added 0.40 g of chloroacetone (6.2 mmoles) according to the procedure described in patent WO 02/18311 A1. The entirety is heated at 75° C. for 22 hours. The reaction medium is then evaporated and washed twice with 15 mL of ethyl acetate.

The finished product is obtained as a viscous brown liquid (0.5 g, 57%).

The spectrometry and spectroscopy results agree with the structure of compound (3).

Example 2

Synthesis of 1-(2-oxo-propyl)-pyridinium toluene-4-sulfonate (Compound 2)

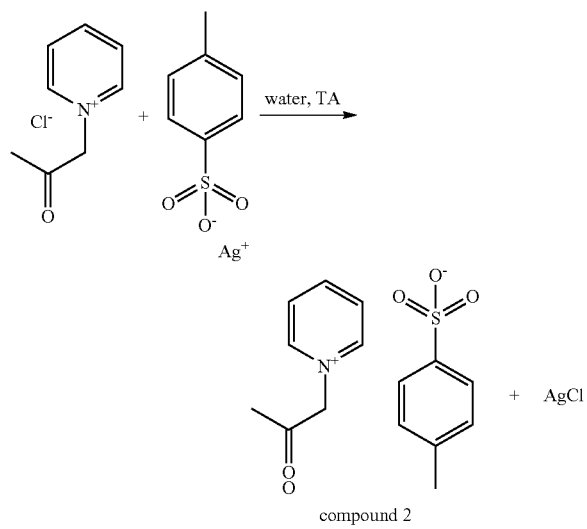

compound 2

To a solution of 7.38 g of 1-(2-oxopropyl)pyridinium chloride (4.3 mmoles) in 40 mL of water is added 12 g silver tosylate (4.3 mmoles). A white precipitate is filtered after 1 h stirring at ambient temperature, protected from light. The filtrate is evaporated to dryness.

The finished product is obtained as a yellow-brown hardening oil (11.4 g, 86%).

The spectrometry and spectroscopy results agree with the structure of compound 2.

Example 3

In this example, the effect of improvement on the oxidizing power produced by the pyridinium salts according to the invention is studied.

I. Preparation of Synthetic Melanin

The synthetic melanin used for the evaluation is obtained by polymerizing 5,6-dihydroxyindole with hydrogen peroxide according to the following procedure:

To 456 g of water heated to 80° C. is added 100 g of 5,6 dihydroxyindole. After 10 minutes of stirring, 1 mL of a 20% aqueous ammonia solution is added then the medium is held for 30 minutes at 80° C. 152 g of 30% hydrogen peroxide is then added dropwise and the stirring is held for 2.5 hours at 80° C. After cooling, the suspension formed is filtered and washed with water.

This yields 86 g of synthetic melanin.

II. Compositions Tested

The compositions used in this example have been obtained from the following ingredients (the percentages indicated are percentages by weight relative to the total weight of the composition).

Compositions B and C are compositions according to the invention.

Comparative composition D comprises the following pyridinium salt:

|  | Composition A | Composition B | Composition C | Composition D |
| --- | --- | --- | --- | --- |
| H2O2 | 6% | 6% | 6% | 6% |
| 1-2-oxo-propyl)pyridinium chloride (compound 1) | — | 36 mg | 15 mg | — |
| 2-acetyl-1-methylpyridinium toluene-4-sulfonate | — | — | — | 36 mg |
| Water | qs 100 | qs 100 | qs 100 | qs 100 |

III. Procedure

The following procedure is applied for each composition described in the table in section II.

To 1 mg synthetic melanin obtained in accordance with section I are added 1 mL of water, 1 mL of aqueous ammonia and ammonium chloride buffer at pH=9.5, and 1 mL of the composition studied (compositions A, B, C and D).

The lightening (L*) obtained after fifty minutes of incubation is measured.

IV. Results

| | Composition A | Composition B | Composition C | Composition D |
|---|---|---|---|---|
| Lightening level (L*) | 36 | 68 | 71 | 62 |

The lightening obtained that is observed is higher for compositions B and C according to the invention than for compositions A and D.

Particularly, the presence of pyridinium salts improving the oxidizing power of hydrogen peroxide and therefore boosting its activity is observed (comparison between composition A and compositions B and C).

Moreover, it is observed that the presence of pyridinium salts according to the invention improves the oxidizing power of hydrogen peroxide compared to a pyridinium salt having a different structure.

The invention claimed is:

1. A method for treating keratin substances, the method comprising applying to the keratin substances at least one compound chosen from compounds represented by formula (I), addition salts thereof, or solvates thereof:

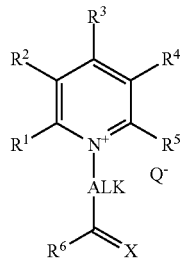

(I)

wherein:
$R^1$, $R^2$, $R^3$, $R^4$ and $R^5$, which may be identical or different, each represent:
  a hydrogen or halogen atom;
  a linear or branched $C_1$-$C_{10}$ alkyl substituent, optionally substituted by one or more hydroxyl, $C_1$-$C_{10}$ alkoxy, $C_1$-$C_4$ hydroxyalkyl and —$NR^7R^8$ groups;
  a linear or branched $C_1$-$C_{10}$ alkoxy substituent, optionally substituted by one or more hydroxyl, $C_1$-$C_{10}$ alkoxy, $C_1$-$C_4$ hydroxyalkyl and —$NR^7R^8$ groups;
  or two adjacent substituents $R^1$ and $R^2$, $R^2$ and $R^3$, $R^3$ and $R^4$ and/or $R^4$ and $R^5$ can form together with the carbon atoms to which they are attached a cycloalkyl group including 5 to 10 members or an aryl group including 6 to 10 members, it being understood that said cycloalkyl or aryl group optionally comprises one or more heteroatoms and is optionally substituted by one or more halogen atoms, one or more linear or branched $C_1$-$C_{10}$ alkyl substituents, one or more linear or branched $C_1$-$C_{10}$ alkoxy substituents, one or more hydroxyl groups, one or more $C_1$-$C_4$ hydroxyalkyl substituents and one or more —$NR^7R^8$ groups;
ALK represents a linear or branched, saturated or unsaturated $C_1$-$C_{10}$ alkyl substituent;
$R^6$ represents:
  a hydrogen or halogen atom,
  a linear or branched, saturated or unsaturated $C_1$-$C_{10}$ alkyl substituent, optionally interrupted by one or more heteroatoms chosen from oxygen and nitrogen and/or optionally substituted by one or more hydroxyl, $C_1$-$C_{10}$ alkoxy, $C_1$-$C_4$ hydroxyalkyl and —$NR^7R^8$ groups;
  an aryl substituent including 5 to 12 members optionally substituted by one or more halogen atoms, one or more linear or branched $C_1$-$C_{10}$ alkyl substituents, one or more linear or branched $C_1$-$C_{10}$ alkoxy substituents, one or more hydroxyl groups, one or more $C_1$-$C_4$ hydroxyalkyl substituents and one or more —$NR^7R^8$ groups;
X represents a heteroatom chosen from an oxygen atom or a sulfur atom, or a —$NR^{11}$ substituent;
$R^7$, $R^8$, and $R^{11}$, which may be identical or different, denote a hydrogen atom or a linear or branched $C_1$-$C_{10}$ alkyl substituent optionally substituted with one or more hydroxyl or $C_1$-$C_{10}$ alkoxy, $C_1$-$C_4$ hydroxyalkyl and amino groups;
  wherein one of the substituents $R^1$ or $R^5$ may form a ring with the substituent $R^6$;
$Q^-$ represents an anion or a mixture of organic or inorganic anions that ensure electroneutrality in compounds of formula (I).

2. The method according to claim 1, characterized in that X represents an oxygen atom.

3. The method according to claim 1, characterized in that ALK represents a linear $C_1$-$C_{10}$ alkylene substituent, a linear $C_2$-$C_{10}$ alkenylene substituent or a linear $C_2$-$C_{10}$ alkynylene substituent.

4. The method according to claim 1, characterized in that the substituents $R^1$ and $R^5$ represent a hydrogen atom.

5. The method according to claim 1, characterized in that the substituents $R^2$ and $R^4$, which may be identical or different, represent a hydrogen atom or a linear $C_1$-$C_4$ alkyl substituent.

6. The method according to claim 1, characterized in that $R^3$ represents a hydrogen atom or a —$COR^{10}$ substituent with $R^{10}$ denoting a linear $C_1$-$C_{10}$ alkyl substituent.

7. The method according to claim 6, characterized in that $R^7$, $R^8$, and $R^{10}$, which may be identical or different, denote a linear or branched $C_1$-$C_{10}$ alkyl substituent optionally substituted with one or more hydroxyl, $C_1$-$C_{10}$ alkoxy and amino groups.

8. The method according to claim 1, characterized in that the at least one compound of formula (I) is chosen from the compounds of formula (II), addition salts thereof, or solvates thereof:

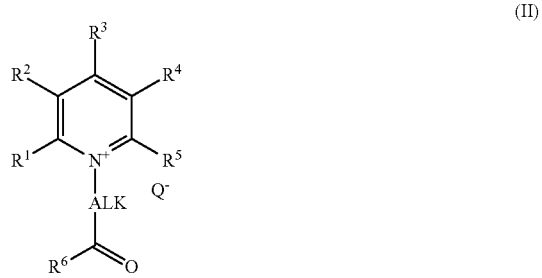

(II)

in which:
R$^1$ and R$^5$ represent a hydrogen atom;
R$^2$ and R$^4$, which may be identical or different, represent:
a hydrogen atom,
a linear or branched C$_1$-C$_{10}$ alkyl substituent, optionally substituted by one or more hydroxyl, C$_1$-C$_{10}$ alkoxy, and —NR$^7$R$^8$ groups,
a linear or branched C$_1$-C$_{10}$ alkoxy substituent, optionally substituted by one or more hydroxyl, C$_1$-C$_{10}$ alkoxy and —NR$^7$R$^8$ groups;
R$^3$ represents:
a hydrogen atom;
a linear or branched C$_2$-C$_{10}$ alkyl substituent, optionally substituted by one or more hydroxyl, C$_1$-C$_{10}$ alkoxy and —NR$^7$R$^8$ groups,
a linear or branched C$_1$-C$_{10}$ alkoxy substituent, optionally substituted by one or more hydroxyl, C$_1$-C$_{10}$ alkoxy, C$_1$-C$_4$ hydroxyalkyl and —NR$^7$R$^8$ groups:
ALK represents a methylene substituent,
R$^6$ represents a methylene substituent,
R$^7$ and R$^8$, which may be identical or different, denote a hydrogen atom or a linear or branched C$_1$-C$_{10}$ alkyl substituent optionally substituted with one or more hydroxyl, C$_1$-C$_{10}$ alkoxy and amino groups;
Q$^+$ represents an anion or a mixture of organic or inorganic anions that ensure electroneutrality in compounds of formula (II).

9. The method according to claim 1, characterized in that the compound(s) of formula (I) are chosen from the following compounds:

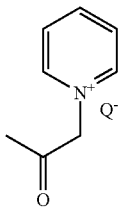

Salt of 1-(2-Oxo-propyl)pyridinium

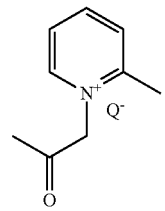

Salt of 2-Methyl-1-(2-Oxo-propyl)-pyridinium and mixtures thereof,
wherein a represents an anion or a mixture of organic or inorganic anions that ensure electroneutrality in said compounds.

10. The method according to claim 1, wherein the method is for improving the oxidizing activity of one or more chemical oxidizing agents.

11. The treatment method according to claim 1, wherein the one or more compounds of formula (I) are applied in the presence of one or more chemical oxidizing agents.

* * * * *

UNITED STATES PATENT AND TRADEMARK OFFICE
CERTIFICATE OF CORRECTION

| | | |
|---|---|---|
| PATENT NO. | : 10,765,615 B2 | Page 1 of 1 |
| APPLICATION NO. | : 15/536731 | |
| DATED | : September 8, 2020 | |
| INVENTOR(S) | : Hercouet et al. | |

It is certified that error appears in the above-identified patent and that said Letters Patent is hereby corrected as shown below:

In the Claims

Column 20, Line 51, please change "(H)" to -- (II) --.

Column 22, Line 25, after "wherein" insert -- Q --.

Signed and Sealed this
Twenty-fourth Day of May, 2022

*Katherine Kelly Vidal*

Katherine Kelly Vidal
*Director of the United States Patent and Trademark Office*